United States Patent
Matsumoto

(10) Patent No.: US 6,585,374 B2
(45) Date of Patent: Jul. 1, 2003

(54) OPHTHALMOLOGIC APPARATUS

(75) Inventor: Kazuhiro Matsumoto, Utsunomiya (JP)

(73) Assignee: Canon Kabushiki Kaisha, Tokyo (JP)

(*) Notice: Subject to any disclaimer, the term of this patent is extended or adjusted under 35 U.S.C. 154(b) by 113 days.

(21) Appl. No.: 09/805,132

(22) Filed: Mar. 14, 2001

(65) Prior Publication Data

US 2001/0028438 A1 Oct. 11, 2001

(30) Foreign Application Priority Data

Mar. 22, 2000 (JP) .................................... 2000-080118
Mar. 22, 2000 (JP) .................................... 2000-080169

(51) Int. Cl.[7] ............................................. A61B 3/14
(52) U.S. Cl. ........................................................ 351/206
(58) Field of Search ................................. 351/205, 206, 351/208, 209, 210, 214, 220, 221

(56) References Cited

U.S. PATENT DOCUMENTS

| | | | |
|---|---|---|---|
| 4,411,502 A | * 10/1983 | Lang et al. ................. | 351/206 |
| 4,820,037 A | 4/1989 | Kohayakawa et al. ...... | 351/211 |
| 4,848,896 A | 7/1989 | Matsumoto ................. | 351/211 |
| 4,952,049 A | 8/1990 | Matsumoto ................. | 351/211 |
| 5,233,372 A | 8/1993 | Matsumoto ................. | 351/221 |
| 5,455,644 A | 10/1995 | Yazawa et al. ............. | 351/206 |
| 5,847,805 A | 12/1998 | Kohayakawa et al. ...... | 351/210 |
| 6,158,864 A | 12/2000 | Masuda et al. ............. | 351/206 |

FOREIGN PATENT DOCUMENTS

| JP | 8-196509 | 8/1996 |
|---|---|---|
| JP | 11-146864 | 6/1999 |

* cited by examiner

Primary Examiner—George Manuel
(74) Attorney, Agent, or Firm—Fitzpatrick, Cella, Harper & Scinto

(57) ABSTRACT

An ophthalmologic apparatus includes a diaphragm, a photo taking system, having a mirror system with a deflection mirror, for taking an eye fundus through the mirror which is disposed in a position nearer to an eye to be examined than to the diaphragm on an optical path, and a controller. The controller controls the photo taking optical system so as to perform photo taking plural times by changing directions of the mirrors, so that a plurality of images for the eye fundus are obtained from a plurality of directions.

20 Claims, 9 Drawing Sheets

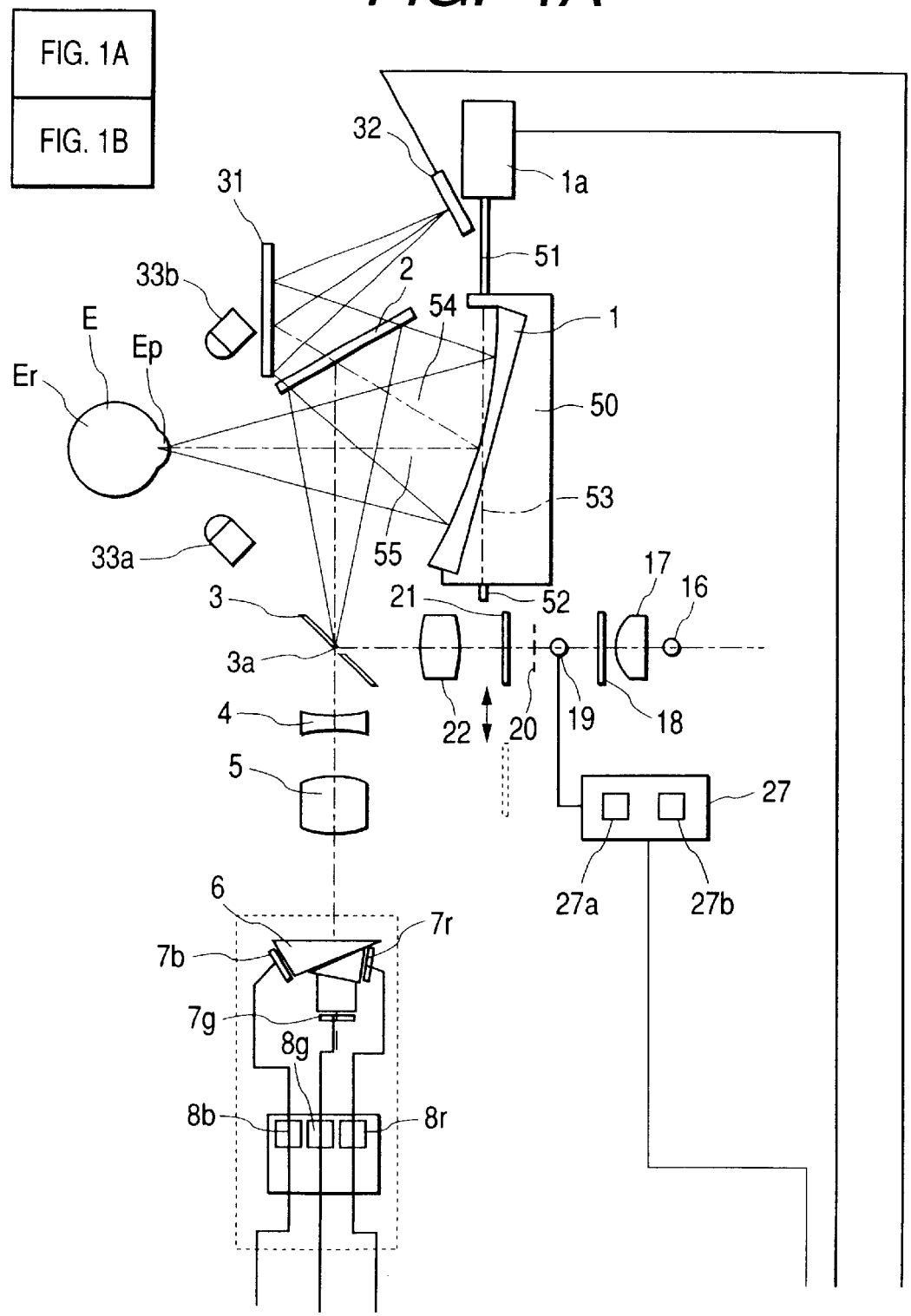

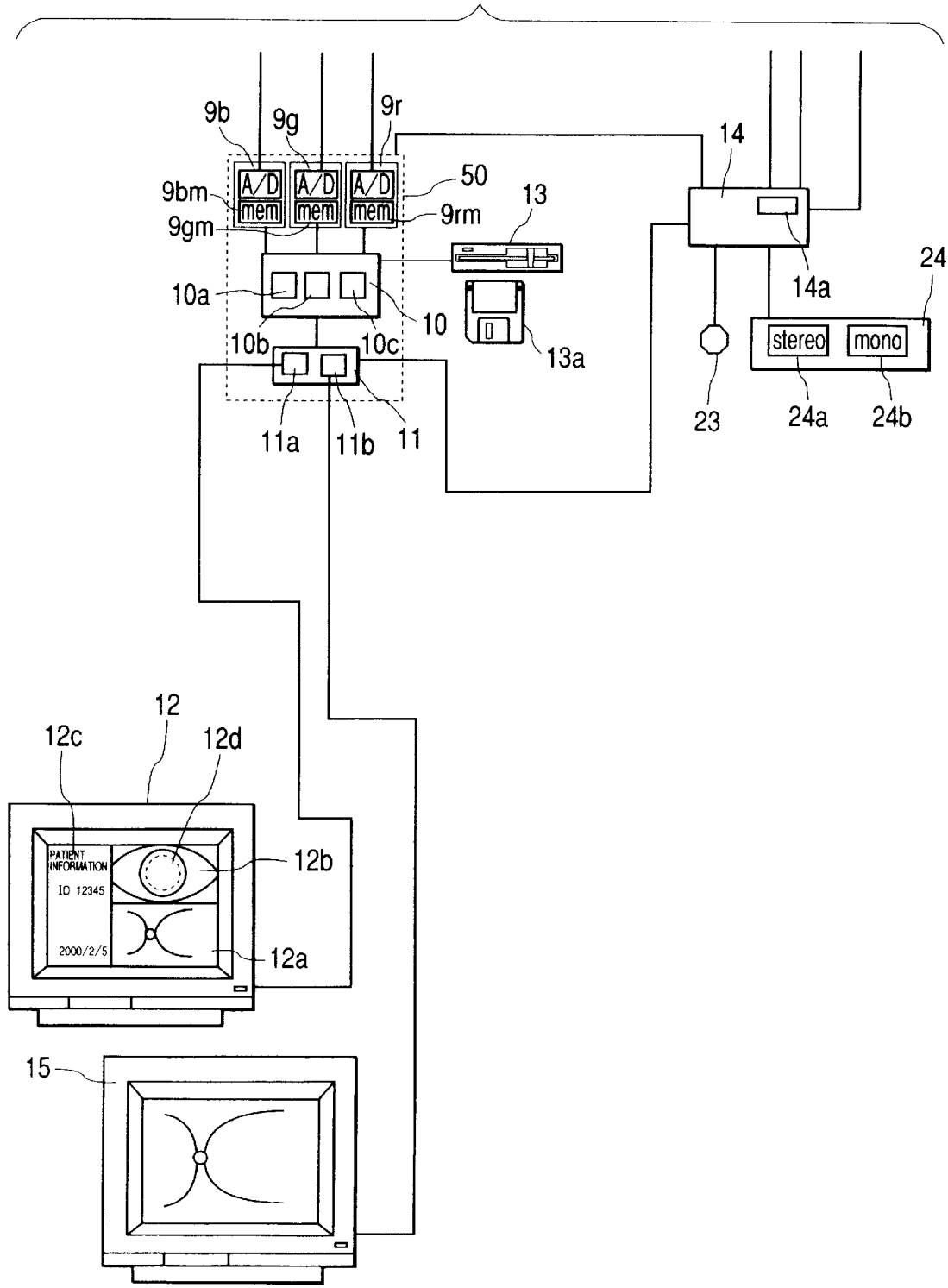

OPHTHALMOLOGIC APPARATUS

BACKGROUND OF THE INVENTION

1. Field of the Invention

The present invention relates to an ophthalmologic apparatus, for example, an eye fundus camera, used in ophthalmology hospitals or the like.

2. Related Background Art

As an example of an ophthalmologic apparatus, there is an apparatus in which stereophotography for an eye fundus of an eye of a person (patient) to be examined can be performed. Generally, the stereophotography has a method of obtaining right and left stereo images simultaneously by photo taking one time and a method of obtaining right and left stereo images by photo taking two times with states where a commonly used photo taking apparatus is shifted to right and left positions. Also, there is a method of obtaining right and left stereo images by changing an angle of parallel flat surface plates disposed between a main mirror and an eye (Japanese Patent Application Laid-Open No. 8-196509). However, the above methods have the following points for improvement.

First, in a simultaneous stereophotography method, since two independent optical systems are required for photo taking of right and left images, the apparatus has a complicated structure and is expensive. Further, since photo taking of the right and left images is performed simultaneously for a pupil limited in size, separation between illumination light and photo taking light is hard, and it is difficult to obtain a wide view angle and a sufficient base length simultaneously.

Second, in a method of obtaining right and left stereo images by photo taking two times with states where a commonly used photo taking apparatus is shifted to right and left positions, a photo taking time is increased. Also, since an interval of time for photo taking of the right and left stereo images is long and a change, for example, rotation occurs in an eye fundus during this interval, it is difficult to obtain precise stereo images.

Third, in a method of performing stereophotography by changing an angle of parallel flat surface plates disposed between a main mirror and an eye, since the moveable flat surface plate is disposed right in front of the main mirror, the limitation on a physical arrangement is large, so that an operation distance of a lens is shortened and operationality during photo taking is deteriorated. Photo taking quality is deteriorated and occurrences of a ghost and a flare are caused due to aberration by the flat surface plate.

Conventionally, in an ophthalmologic apparatus, for example, in an eye fundus camera for photo-taking an eye fundus of a person to be examined, alignment between the pupil and an optical system at photo taking is commonly performed by an operator manually. An apparatus, which is obtained by improving the above apparatus, for performing automatic alignment by actuating an entire optical system in up, down, right and left directions or in an optical axis direction is known (Japanese Patent Application Laid-Open No. 11-146864). However, the above apparatus has the following points for improvement.

First, since in an ophthalmologic apparatus such as an eye fundus camera the number of adjustment or determination items, such as a position relationship between the pupil and the optical system, an operation distance in an optical axis direction, focusing of the eye fundus and a photo taking range of the eye fundus, is large, adjustment operation by hand cannot be performed easily.

Second, in an apparatus for performing automatic alignment by actuating an entire optical system, it is difficult to actuate the optical system with large weight rapidly. Thus, rapid tracking of the optical system to movement of the eye can not be performed easily. This causes the size of the apparatus to be large and the cost to be high.

SUMMARY OF THE INVENTION

Main object of the present invention is to improve a conventional ophthalmologic apparatus. One concrete object is to provide an excellent ophthalmologic apparatus in which stereo eye fundus images of the eye can be obtained suitably. One further concrete object is to provide an ophthalmologic apparatus in which stereophotography can be performed with extremely high precision, regardless of a structure in which the number of movable portions is small and which is simple and has high reliability, that is, an ophthalmologic apparatus in which both high reliability and high precision can be attained with high grade.

To attain the above object, according to one aspect of the present invention, there is provided an ophthalmologic apparatus comprising a diaphragm, a photo taking system, having a mirror system with a deflection mirror, for taking an eye fundus image through the mirror which is disposed in a position nearer to an eye to be examined than to the diaphragm in an optical path, and a controller for controlling the photo taking system so as to perform photo taking plural times by changing directions of the mirror, thereby obtaining a plurality of images for the eye fundus from a plurality of directions.

Another object of the present invention is to provide an excellent ophthalmologic apparatus in which eye fundus images of the eye can be obtained suitably. A further concrete object is to provide an ophthalmologic apparatus in which photo taking can be performed with extremely high precision by alignment with high speed and high precision, regardless of a structure in which the number of movable portions is small and which is simple and has high reliability, that is, an ophthalmologic apparatus in which both high reliability and high precision can be attained with high grade.

To attain the above object, according to another aspect of the present invention, there is provided an ophthalmologic apparatus comprising a diaphragm, a photo taking system, having a mirror system with a deflection mirror, for taking an eye fundus image through the mirror which is disposed in a position nearer to an eye to be examined than to the diaphragm in an optical path, and a light source for leading light to the eye fundus of the eye through the mirrors to illuminate the eye fundus.

Further objects of the present invention and embodiments thereof are clear in explanation of the embodiments below.

BRIEF DESCRIPTION OF THE DRAWINGS

FIG. 1 is comprised of FIGS. 1A and 1B showing a structure of an eye fundus camera according to a first embodiment of the present invention;

Figure 2:
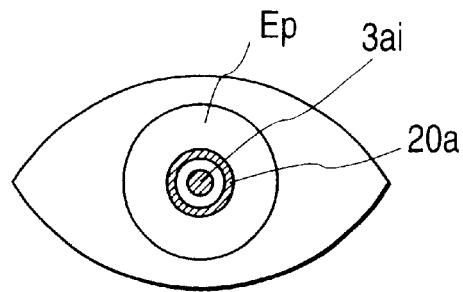
FIG. 2 shows a relationship between an pupil and a stop.

DESCRIPTION OF THE PREFERRED EMBODIMENTS (First Embodiment)

FIGS. 1A and 1B show an embodiment of a stereophotograph eye fundus camera in which stereophotography and monophotography for eye fundus can be selected. On an optical path, an objective reflecting optical system is constructed by a mirror system. This mirror system includes a main mirror 1 which is a total reflection mirror and a sub mirror 2 for transmitting only near-infrared light and reflecting visual light and infrared light, and the main mirror 1 and the sub mirror 2 are disposed in succession before an eye E of a patient. Also, a photo taking optical system for an eye fundus has a diaphragm 3 which is a partially holed mirror, a focal lens 4 movable on an optical axis, a photo taking lens 5, a color separation prism 6 and image pickup elements 7b, 7r and 7g. In the diaphragm 3, a hole 3a is formed. The diaphragm 3 has a function as a partially holed mirror and a function as a diaphragm.

Here, the main mirror 1 is a concave mirror having a concave reflection surface for imaging a reflected image with respect to the diaphragm 3a by the sub mirror 2 onto the vicinity of a pupil Er. A shape of the reflection surface is a curved surface to image the reflected image on the pupil Er. The main mirror 1 is held by a holder 50 supported physically by a hinge 51 for supporting an upper portion and a hinge 52 for supporting a lower portion. A straight line joining the hinge 51 with the hinge 52 defines a virtual rotation axis 53. The holder 50 (the main mirror 1) can be rotary-deflected about the rotation axis 53 as a standard. As shown in FIGS. 1A and 1B, the reflection surface of the main mirror 1 is slanted with respect to the rotation axis 53, and the main mirror 1 is located so as to approximately align an optical axis of an incident light 54 with a cross point between the reflection surface and the rotation axis 53. A reflected light 55 from the reflection surface of the main mirror 1 is led onto the pupil Ep. An angle formed by the optical axis of the reflected light 55 and the rotation axis 53 is about a right angle. The rotation axis 53, the optical axis of the incident light 54 and the optical axis of the reflected light 55 are all included within the same plane (a plane of Drawing sheet of FIGS. 1A and 1B).

The main mirror 1 is deflected by a stepping motor 1a as an actuator, so that an angle of the reflection surface can be changed. Here, an actuator is not limited to the stepping motor. An another motor, a solenoid, a structure in which a piezoelement is disposed on a back surface of a mirror, or the like can be used as a variation example.

Color separation of red, blue and green is made by the color separation prism 6. Infrared light and red light are led to the image pickup element 7r, blue light is led to the image pickup element 7b, green light is led to the image pickup element 7g, and then each intensity is detected. Signals outputted from these image pickup elements are amplified by amplifiers 8b, 8r and 8g which are color balance adjusting means and can change an amplification factor of each color individually, and then are inputted to an imaging unit 50. The imaging unit 50 is constructed by A/D convertor 9b, 9r and 9g for converting an analog signal into a digital signal, image memories 9bm, 9rm and 9gm for storing digital image data, an image processor 10 for adjusting a distortion of an image, and video RAMs 11a and 11b. A storage device 13 is connected with the image processor 10 and controlled by a controller 14. The storage device 13 has a drive apparatus for an MO, an MD, a DVD, a hard disk, a VCR or the like and performs writing and readout to a recording medium 13a. A display unit 12 displays contents of the video RAM 11a. A stereo display unit 15 performs a 3D-display such that the contents of the video RAM 11a can be observed stereoscopically.

An optical system for illuminating an eye fundus has an observing light source 16, for example, a halogen lamp, for emitting visual light and infrared light as steady light, a condenser lens 17, a visual light cutoff filter 18 for cutting off visual light and transmitting infrared light, a stroboscopic light source 19 for emitting flash light, a stop 20 having a ring shaped aperture, a filter 21 which is disposed to be insertable and removable and cuts off infrared light, a relay lens 22, the diaphragm 3 and the objective reflecting optical system (the main mirror 1 and the sub mirror 2). Also, in order to observe a front eye portion of an eye to be examined, an observing optical system is constructed by a mirror 31, an image pickup element 32 and illuminating light sources 33a and 33b for emitting near-infrared light. A photo taking switch 23 is connected with the controller 14. The stroboscopic light source 19 as a photo taking light source is controlled for light emission by a stroboscopic circuit 27 having a first capacitor 27a and a second capacitor 27b.

Figure 5:
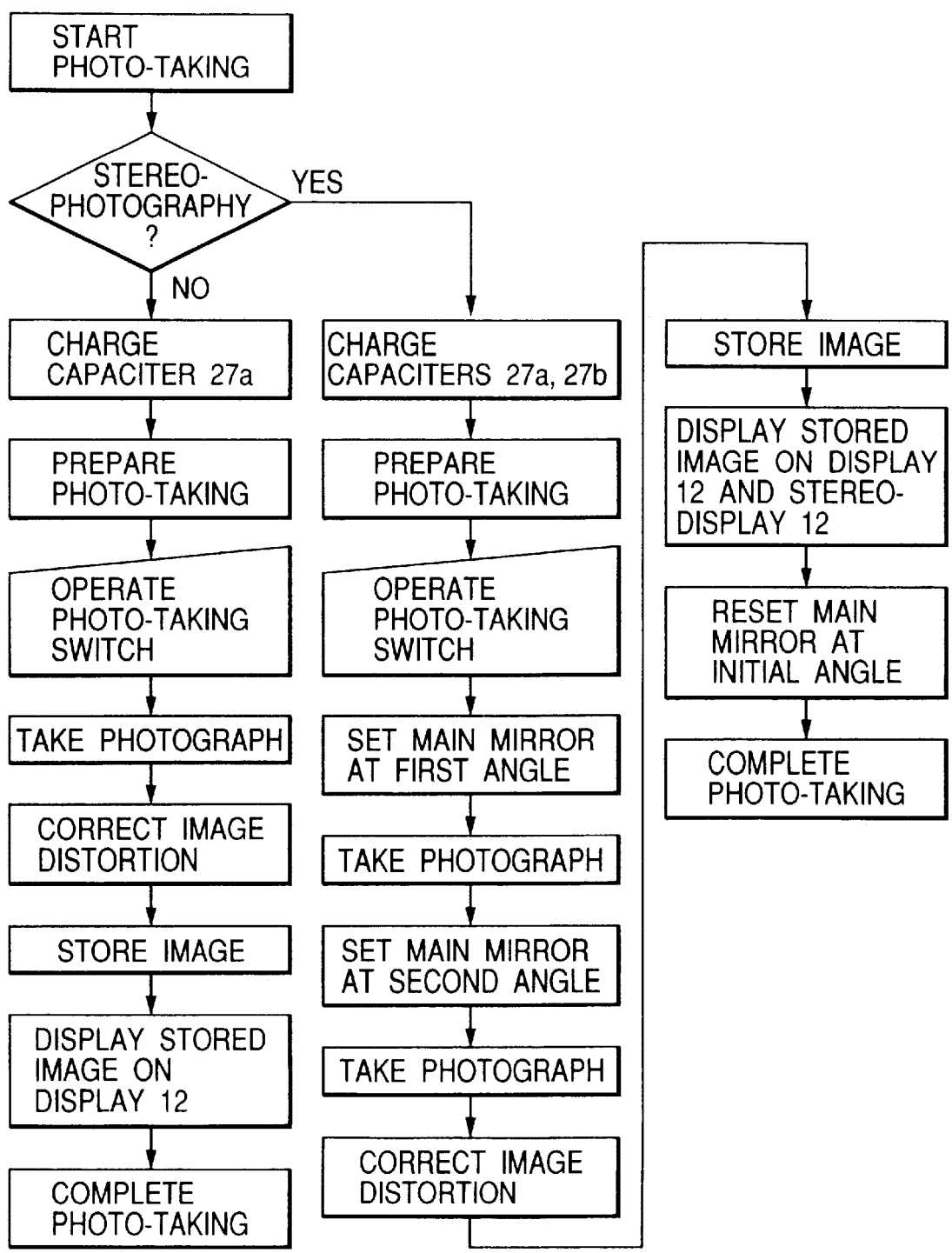
FIG. 5 is a flow chart representing a procedure of photo taking.

Operation of the apparatus with the above structure will be explained below. FIG. 5 is a flow chart representing a procedure of photo taking. First, the case where common monophotography to an eye fundus is performed will be explained. When monophotography is performed, a button 24b of a switch 24 for selecting either monophotography or stereophotography is pushed to input a command. When this command is received, the controller 14 causes only the capacitor 27a to be charged. An operator causes a person to be examined to sit in front of the eye fundus camera, and then performs an alignment between an eye and the eye fundus camera while observing an eye fundus with infrared light. In an observation state, the filter 21 is to be removed from an optical path. Light emitted from the observing light source 16 is condensed by the condenser lens 17, and only infrared light of the condensed light is transmitted by the visual light cutoff filter 18. The infrared light is passed through the photo taking light source 19, the aperture of the stop 20 with the ring shaped aperture and the relay lens 22, reflected upward by a mirror portion located in the vicinity of the diaphragm 3, and passed through the sub mirror 2, the main mirror 1 and the eye pupil Ep to illuminate the eye fundus Er. Light from the eye fundus Er illuminated with the infrared light is reversed with the same optical path, passed through the diaphragm 3, the focal lens 4 and the photo taking lens 5, and is incident into the color separation prism 6 to extract the infrared light. With the extracted infrared light, an infrared eye fundus image is imaged on the image pickup element 7r and converted into an electric signal. This signal is amplified by the amplifier 8r, inputted to the imaging unit 50, written in a portion of the video RAM 11a corresponding to an area 12a of the display unit 12, and thus displayed on the area 12a of the display unit 12. Also, a front eye portion image is displayed on an area 12b of the display unit 12. A front eye portion is illuminated with near-infrared light (having a wavelength of 720 nm) emitted from the illuminating light source. An image of the front eye portion illuminated is reflected by the main mirror 1, passed through the sub mirror 2, reflected by the mirror 31 again, and imaged on an image pickup surface of the image pickup element 32 for pickup of the front eye portion. A signal from the image pickup element 32 is inputted to the controller 14, converted into a digital signal, and written in a portion of the video RAM 11a corresponding to the area 12b of the display unit 12. The front eye portion image and the eye fundus image are displayed simultaneously on the display unit 12 in separate areas. While observing the front eye portion image displayed on the area 12b of the display unit 12, the operator performs alignment of an optical system in up and down directions and right and left directions using an operation means (not shown) such that the pupil and an index 12d become a concentric state, and further performs alignment of the optical system in an optical axis direction such that focusing to a pattern of an iris of the person to be examined is made suitable. Also, the operator observes the eye fundus image displayed on the area 12a, performs focusing by actuating the focal lens 4, and then determines a photo taking range.

After the above photo taking preparation is completed, the operator operates the photo taking switch 23 to perform static photo taking. When a command inputted by the photo taking switch 23 is detected, the controller 14 inserts the filter 21 for cutting off infrared light into an optical path, causes the image pickup elements 7r, 7g and 7b to start light storage, and outputs a light emitting signal to the stroboscopic circuit 27 to perform photo taking. The stroboscopic circuit 27 which receives the light emitting signal outputs a trigger signal to the stroboscopic light source 19 for light emission which arises from discharge of electric charge charged in the first capacitor 27a. Similar to the case of the above observation light, flash light from the stroboscopic light source 19 is passed through the aperture of the stop 20, and infrared light of the flash light is cut off by the filter 21. Remaining visual light is passed through the relay lens 22, reflected to the left by a mirror portion located in the vicinity of the hole 3a of the diaphragm 3, and passed through the sub mirror 2 and the main mirror 1 to illuminate the eye fundus Er through the ring-shaped region 20a on the pupil Ep as shown in FIG. 2. An image of the eye fundus thus illuminated is passed through a center portion of the pupil as shown in FIG. 2, and again passed through the main mirror 1, the diaphragm 3, the focal lens 4 and the photo taking lens 5. Then, this image is incident into the color separation prism 6, separated into red, green and blue, imaged in the image pickup elements 7r, 7g and 7b, and converted into electric signals. The amplifiers 8r, 8g and 8b amplify these signals by predetermined amplification factors for each color to adjust color balance. In image boards 9r, 9g and 9b, these electric signals are converted into digital image data by an A/D converter portion, and the image data is stored in the image memories 9rm, 9gm and 9bm as memory means in the image board 9. The image data is corrected with respect to image distortion by the image processor 10 in accordance with a pattern stored in a memory 10a. The corrected image data is stored in a memory 10b, recorded in the recording medium 13a by the storage device 13, and displayed on the area 12a of the display unit 12. Then, the controller 14 causes the filter 21 to be removed from the optical path, so that monophotography is completed.

Next, the case where stereophotography to an eye fundus is performed will be explained. With respect to a basic operation procedure, an angle of the main mirror is changed into a predetermined angle by control means and a light source is light-emitted plural times (twice) in synchronization with this change, so that a plurality of images are obtained with different directions.

When stereophotography is performed, the operator pushes the button 24a of the switch 24 to input a command. The controller 14 which receives this command causes both of the capacitors 27a and 27b to be charged. While observing an eye fundus of a person to be examined sitting in front of the eye fundus camera with infrared light, the operator performs alignment between an eye and the eye fundus camera. Light emitted from the observing light source 16 is condensed by the condenser lens 17 and only infrared light of the condensed light is transmitted by the visual light cutoff filter 18. The infrared light is passed through the photo taking light source 19, the aperture of the stop 20 with the ring shaped aperture and the relay lens 22, reflected upward by a mirror portion located in the vicinity of the diaphragm 3, and passed through the sub mirror 2, the main mirror 1 and the eye pupil Ep to illuminate the eye fundus Er. Light from the eye fundus Er illuminated with the infrared light is reversed with the same optical path, passed through the diaphragm 3, the focal lens 4 and the photo taking lens 5, and is incident into the color separation prism 6. Infrared light from the color separation prism 6 is imaged on the image pickup element 7r and converted into an electric signal. This signal is amplified by the amplifier 8r with a predetermined amplification factor, inputted to the imaging unit 50, written in a portion of the video RAM 11a corresponding to the area 12a of the display unit 12, and thus displayed on the area 12a of the display unit 12. Also, a front eye portion image is displayed on the area 12b of the display unit 12, similar to the case of monophotography. The front eye portion image and the eye fundus image are displayed simultaneously on the display unit 12.

While observing the front eye portion image displayed on the area 12b of the display unit 12, the operator performs alignment of an optical system in up and down directions and right and left directions using an operation device (not shown), for example, a joystick, such that the pupil image and the index 12d to be displayed by synthesizing with the pupil image become a concentric state, and further performs alignment of the optical system in an optical axis direction such that focusing to a pattern of an iris of the person to be examined is made suitable. Also, the operator observes the eye fundus image displayed on the area 12a, performs focusing by actuating the focal lens 4, and then determines a photo taking range.

After the above photo taking preparation is completed, the operator operates the photo taking switch 23 to perform static image stereophotography. When the controller 14 detects a command inputted by the photo taking switch 23, it inserts the filter 21 for cutting off infrared light into an optical path, and drives the stepping motor 1a to set the main mirror 1 to be a first predetermined angle for stereophotography. In synchronization with this, the controller 14 cause the image pickup elements 7r, 7g and 7b to start light storage, and outputs a light emitting signal to the stroboscopic circuit 27 to perform a first photo taking in stereophotography.

Figure 3:
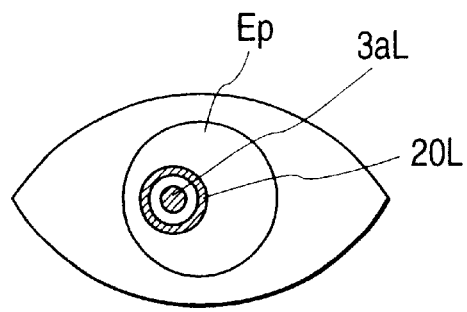
FIG. 3 shows a relationship between an pupil and a stop.
Figure 4:
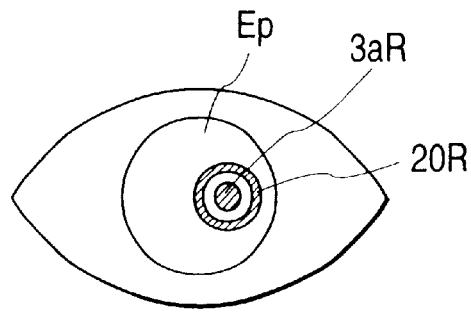
FIG. 4 shows a relationship between an pupil and a stop.

Here, an angle of the main mirror and a stop position on a pupil will be explained. FIG. 2 shows a positional relationship between a pupil and a stop when alignment is completed. A pupil image and a stop image are located concentrically. At this time, a mirror is disposed in an initial position and is not slanted with respect to the rotation axis 53. FIG. 3 shows a positional relationship between a pupil and a stop in the case of stereophotography with a first mirror angle. On the pupil, the stop is eccentric to left side. FIG. 4 shows a positional relationship between a pupil and a stop in the case of stereophotography with a second mirror angle. On the pupil, the stop is eccentric to right side. An eccentric amount of the stop in FIG. 4 with respect to a position of the stop in FIG. 3 corresponds to a base line length. The stroboscopic circuit 27 which receives the light emitting signal outputs a trigger signal to the stroboscopic light source 19 for light emission which arises from discharge of electric charge charged in the first capacitor 27a. Similar to the case of the above observation light, a light flux from the stroboscopic light source 19 is passed through the aperture of the stop 20 with the ring shaped aperture, and infrared light of the light flux is cut off by the filter 21. Remaining visual light is passed through the relay lens 22, reflected to the left by a mirror portion located in the vicinity of the diaphragm 3, and passed through the sub mirror 2 and the main mirror 1 to illuminate the eye fundus Er from a position 20L which is eccentric to the left side from the center of the pupil Ep as shown in FIG. 3. An image of the eye fundus thus illuminated is passed through an imaging position 3aL of the diaphragm 3 which is eccentric to the left side from the center of the pupil as shown in FIG. 3, and again passed through the main mirror 1, the diaphragm 3, the focal lens 4 and the photo taking lens 5. Then, this image is incident into the color separation prism 6, separated into red, green and blue, and imaged in the image pickup elements 7r, 7g and 7b. The amplifiers 8r, 8g and 8b amplify the signals from the image pickup elements by predetermined amplification factors for each color to adjust color balance. In the image boards 9r, 9g and 9b, the signals are converted into digital image data by an A/D converter portion and stored in the image memories 9rm, 9gm and 9bm. The image data is corrected with respect to image distortion by the image processor 10 in accordance with a correction pattern stored in the memory 10a. The corrected image data is stored in the memory 10b.

A second photo taking in stereophotography is performed subsequent to the above operation. The controller 14 causes the main mirror 1 to set a mirror angle into a second predetermined angle different from the first predetermined angle. In synchronization with this, the controller 14 outputs a signal to the stroboscopic circuit 27. The stroboscopic circuit 27 outputs a trigger signal to the stroboscopic light source 19 for light emission which arises from discharge of electric charge charged in the capacitor 27b. Light from the stroboscopic light source 19 is passed through the same optical path as that mentioned above to illuminate the eye fundus Er from a position 20R which is eccentric to the right side from the center of the pupil Ep as shown in FIG. 4. An image of the eye fundus thus illuminated is passed through an imaging position 3aR of the diaphragm 3 which is eccentric to the right side from the center of the pupil as shown in FIG. 4, and again passed through the main mirror 1, the diaphragm 3, the focal lens 4 and the photo taking lens 5. Then, this image is incident into the color separation prism 6, separated into red, green and blue, imaged in the image pickup elements 7r, 7g and 7b and converted into electric signals. The amplifiers 8r, 8g and 8b amplify these signals by predetermined amplification factors for each color to adjust color balance. In the image boards 9r, 9g and 9b, the signals are converted into digital image data by an A/D converter portion and stored in the image memories 9rm, 9gm and 9bm. The image processor 10 corrects the image data with respect to image distortion in accordance with a correction pattern stored in the memory 10a to store the corrected image data into a memory 10C.

Images stored in the memories 10b and 10c are recorded in the recording medium 13a by the storage device 13. Simultaneously, these images are written in a portion of the video RAM 11a corresponding to the areas 12a and 12b and displayed on the display unit 12 individually. Also, these images are written in a portion of the video RAM 11b for stereo display and thus displayed on a stereo display unit 15. Therefore, the operator can observe a stereo eye fundus image displayed on the stereo display unit 15. Further, by observing right and left images displayed individually on the display unit 12, flare and a difference of brightness of an image can be determined about each image. After the photo taking is completed, the controller 14 causes the main mirror 1 to return to an initial position and causes the filter 21 to remove from the optical path.

In the above example, although the case of a constant base line length is explained, means for selecting a base line length and means for changing an angle to slant the main mirror in accordance with the selected base line length may be provided. Even if a radius of a pupil of an eye is short, a fine stereo image can be obtained. Thus, it is convenient for the operator. Also, in the above example, although a deflection angle of the main mirror 1 is changed to perform stereophotography with the right and the left, instead of this, a deflection angle of the sub mirror 2 may be changed. Since the sub mirror 2 has a small size, it is suitable for quick actuation. Both the main mirror 1 and the sub mirror 2 may be deflected by rotation axes with different directions each other. In short, at least one mirror of the objective reflecting optical system may be deflected such that eye fundus images can be obtained with different directions.

The apparatus mentioned above has the following advantages:

(1) By changing angles of the objective mirrors, stereophotography for the eye fundus image with a wide angle of view can be performed with a sufficient base line length.

(2) Since stereophotography can be performed with operation once, operation is simple and a stereo image with high precision can be obtained.

(3) The stereophotography can be performed by using a simple structure, for example, by actuating mirrors. Thus, without complicating a common monophotography apparatus, an apparatus capable of performing monophotography and stereophotography with one operation can be provided. As a result, it is unnecessary to use two eye fundus cameras for the operator.

(4) By actuating mirrors by only a minute amount, photo taking with different directions can be performed plural times. Also, since the number of movable portions is small, stereophotography can be performed with extremely short photo taking interval in which a displacement of the eye boll can be disregarded.

(5) Since the objective lenses are used, it is unnecessary to arrange a block point plate or the like, and an illuminating optical system can be miniaturized. Also, since it is unnecessary to replace a block point in monophotography and stereophotography, a structure is simple and reliability is further improved.

(Second Embodiment)

Figure 6:
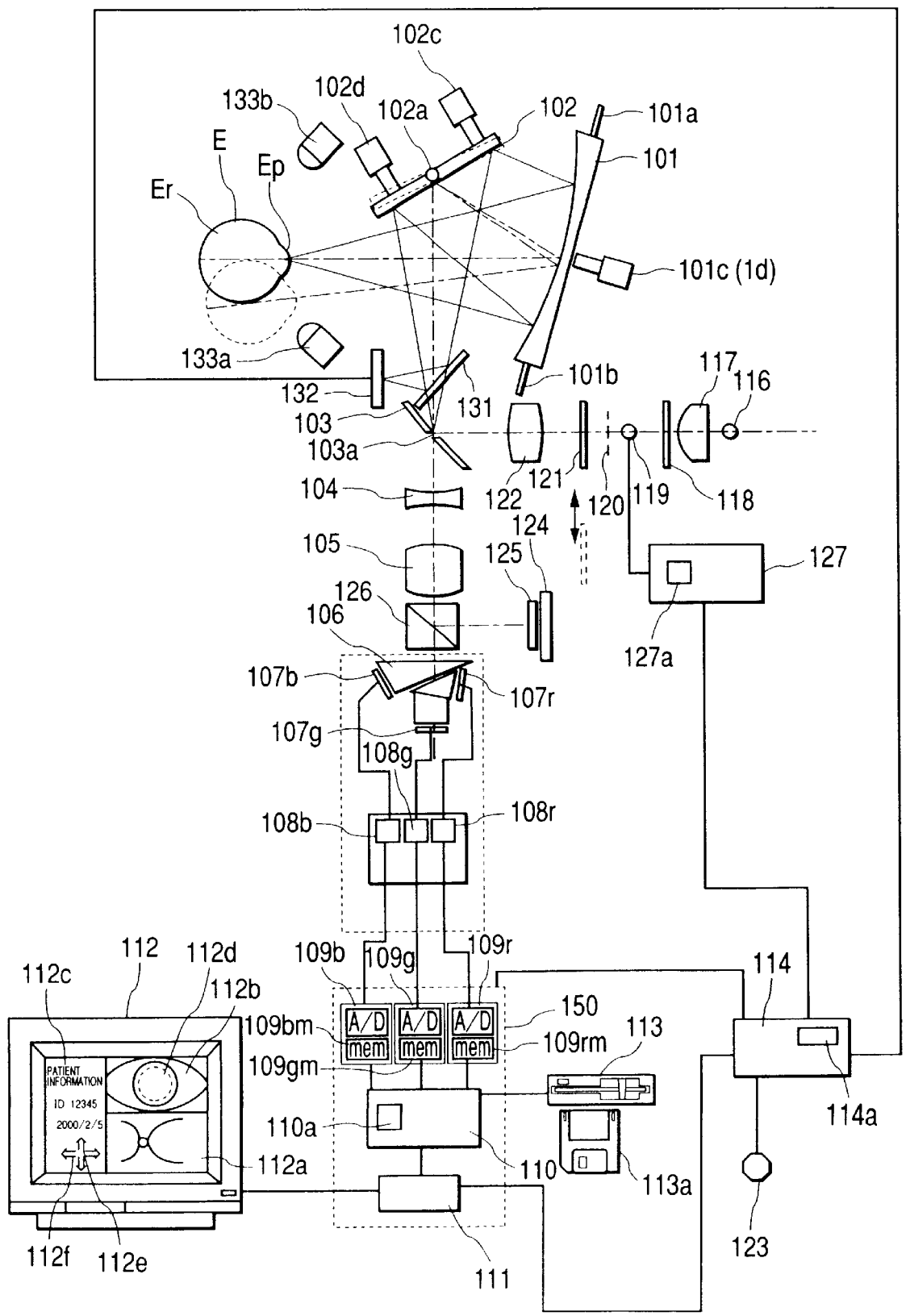
FIG. 6 shows a structure of an eye fundus camera according to a second embodiment of the present invention.

FIG. 6 shows another embodiment of an eye fundus camera. On an optical path, an objective reflecting optical system is constructed by a main mirror 101 and a sub mirror 102 which are disposed in succession before an eye E. These mirrors together are a total reflection mirror. Also, a photo taking optical system for an eye fundus has a diaphragm 103 which is a partially holed mirror, a focal lens 104 movable on an optical axis, a photo taking lens 105, a color separation prism 106 and image pickup elements 107b, 107r and 107g. In the diaphragm 103, a hole 103a is formed. The diaphragm 103 has a function as a partially holed mirror and a function as a diaphragm.

Here, the main mirror 101 has a reflection surface which is a portion of a curved surface to image the reflected image of the diaphragm 103 by the sub mirror 102 on the pupil. The main mirror 1 is supported rotatably with hinges 101a and 101b, assuming, as a rotation axis, a straight line formed by a plane having two focal points and an optical axis and a tangent plane in a contact point between the curved surface and the optical axis. Also, two motors 101c and 101d as actuators are disposed in right and left directions on a back surface of the main mirror 101. Gears (not shown) are coupled with the rotation axes of the motors 101c and 101d. The gears convert the rotation operation of the rotation axes of the motors into operation of an axis direction to push and pull the main mirror 101, so that a rotation angle, that is, a deflection state is controlled. On the other hand, the sub mirror 102 is supported rotatably with hinges 102a and 102b, assuming, as a rotation axis, a straight line which is vertical to a plane including an optical axis reflected by the sub mirror 102 and passes a reflection point on the optical axis. Also, two motors 102c and 102d as actuators are disposed in up and down directions on a back surface of the sub mirror 102. Gears (not shown) are coupled with the rotation axes of the motors 102c and 102d. The gears convert the rotation operation of the rotation axes of the motors into operation of an axis direction to push and pull the sub mirror 102, so that a rotation angle is controlled.

Color separation of red, blue and green is made by the color separation prism 106. Infrared light and red light are led to the image pickup element 107r, blue light is led to the image pickup element 107b and green light is led to the image pickup element 107g, and then each intensity is detected. Signals output from these image pickup elements are amplified by the amplifiers 108b, 108r and 108g which are color balance adjusting devices and can change an amplification factor of each color individually, and then inputted to an imaging unit 150. The imaging unit 150 is constructed by A/D convertor 109b, 109r and 109g for converting an analog signal into a digital signal, image memories 109bm, 109rm and 109gm for storing digital image data, an image processor 110 for adjusting a distortion of an image, and a video RAM 111. A storage device 113 is connected with the image processor 110 and controlled by a controller 114. The storage device 113 has a drive apparatus for an MO, an MD, a DVD-RAM, a hard disk, a VTR tape or the like and performs writing to and readout from a recording medium 113a. A display unit 112 displays the contents of the video RAM 111.

An optical system for illuminating an eye fundus has an observing light source 116, for example, a halogen lamp for emitting visual light and infrared light as steady light, a condenser lens 117, a visual light cutoff filter 118 for cutting off visual light and transmitting infrared light, a stroboscopic light source 119 for emitting flash light, a stop 120 having a ring shaped aperture, an infrared light cutoff filter 121 which is disposed to be insertable and removable and cuts off infrared light, a relay lens 122, the diaphragm 103 and the objective reflecting optical system (the main mirror 101 and the sub mirror 102). Also, in order to indicate a fixed mark to a person to be examined, a fixed mark projecting system is constructed by a backlight 124, a liquid crystal display element 125 and a beam splitter 126. Further, in order to detect a position of a pupil, a mirror 131, an image pickup element 132 for pickup of a front eye portion and illuminating light sources 133a and 133b for emitting near-infrared light are disposed. A photo taking switch 123 is connected with the controller 114. The stroboscopic light source 119 as a photo taking light source is controlled for light emitting by a stroboscopic circuit 127 having a capacitor 127a.

Figure 9:
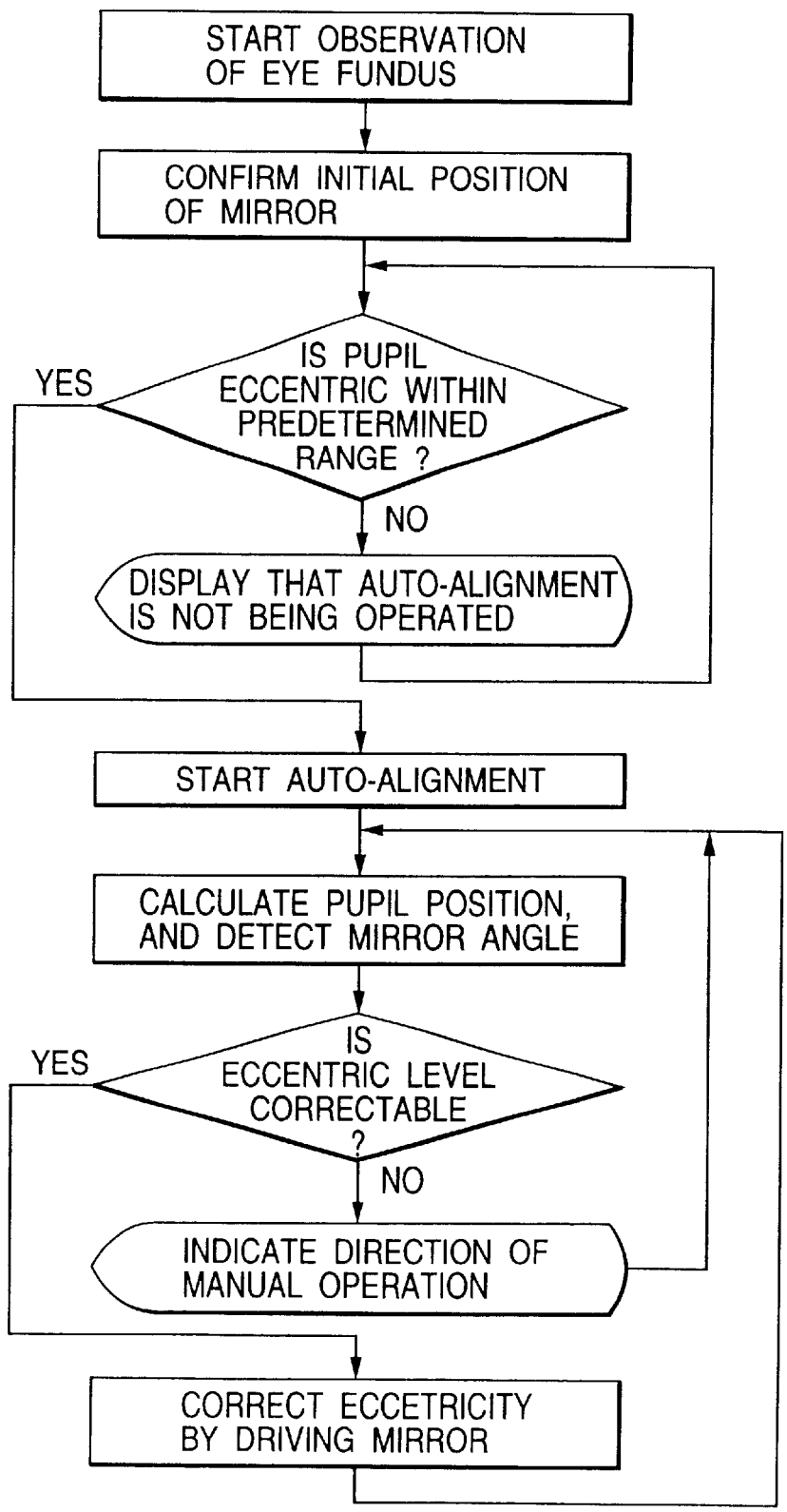
FIG. 9 is a flowchart of operation of the eye fundus camera.

Here, operation of the apparatus with the above structure will be explained below. FIG. 9 shows a flow chart representing a procedure of the operation mentioned above. While observing an eye fundus of a person to be examined sitting in the front of the eye fundus camera with infrared light, the operator performs an alignment between an eye and the eye fundus camera. In an observation state, the filter 121 is to be removed from an optical path. Light emitted from the observing light source 116 is condensed by the condenser lens 117 and only infrared light of the condensed light is transmitted by the visual light cutoff filter 118. The infrared light is passed through the photo taking light source 119, and the aperture of the stop 120 with the ring shaped aperture, and through the relay lens 122, to be reflected upward by a mirror portion located in the vicinity of the diaphragm 103, and passed through the sub mirror 102, the main mirror 101 and the eye pupil Ep to illuminate the eye fundus Er. Light from the eye fundus Er illuminated with the infrared light is reversed in the same optical path, passed through the diaphragm 103, the focal lens 104 and the photo taking lens 105, and is incident into the color separation prism 106 to extract infrared light. By the extracted infrared light, an infrared eye fundus image is imaged on the image pickup element 107r and converted into an electric signal. This signal is amplified by the amplifier 108r, input to the imaging unit 150, written in a portion of the video RAM 111 corresponding to an area 112a of the display unit 112, and thus displayed on the area 112a of the display unit 112. A front eye portion image is displayed on the area 112b of the display unit 112, and illuminated with near-infrared light (having a wavelength of 720 nm) emitted from the illuminating light source. An image of the illuminated front eye portion is reflected by the main mirror 101 and the sub mirror 102, reflected by the wavelength selecting mirror 131 again, and imaged on an image pickup surface of the image pickup element 132. A signal from the image pickup element 132 is inputted to the controller 114, converted into a digital signal, and written in a portion of the video RAM 111 corresponding to the area 112b of the display unit 112. Thus, the front eye portion image and the eye fundus image are displayed simultaneously on the display unit 112 in separate areas. The controller 114 determines that an angle of the main mirror 101 is in an initial neutral position and automatically detects the position of the pupil based on the signal output from the image pickup element 132. That is, the image pickup element 132 is operated as a detector for detecting movement of the eye. Of the image of the front eye portion illuminated by the illuminating light sources 133a and 133b, the image of the pupil is displayed darkly. This image is binary-processed by an image processing technique, so that a continuous portion with a value lower than a predetermined value is recognized as the pupil and the position of the pupil is detected. When it is recognized that the position of the pupil enters within an area where a position can be adjusted by the mirrors, the auto alignment is started in accordance with the movement of the eye. When the pupil is eccentric downward, the controller 114 drives the motor 102d in a direction pushing the sub mirror 102 from a back surface thereof and drives the motor 102c in a direction pulling the sub mirror 102 from the back surface, so that the sub mirror 102 is rotated with the hinges 102a and 102b as rotation axes. When the position of the pupil is eccentric to a right direction or a left direction, the controller 114 drives the motors 102c and 102d to rotate the main mirror 101 with the hinges 101a and 101b as rotation axes. The controller 114 repeats this operation until the pupil image is located in a predetermined position of a center portion of the image pickup element 132. Thus, an alignment is performed always such that a photo taking optical axis passes the center of the pupil. Although once the pupil enters within a predetermined area and then an automatic alignment is started, when a position of the eye is changed largely and an adjustment margin with respect to the angles of the mirrors is not allowed and the alignment can not be performed, characters 112e and 112f as indexes are displayed on the display unit 112. For example, when the character 112f representing an arrow of a left direction is displayed, the operator causes an optical system to actuate to the left using an operation device (not shown). When the character 112e representing an arrow of an upper direction is displayed, the operator causes the optical system to actuate upward using the operation device (not shown). Since minute movement is tracked automatically by driving the mirrors, the operations may be performed with relatively slow movement.

During this alignment operation, the person to be examined gazes a fixed target. The liquid crystal display element has one transmitting portion. An image due to the transmitting portion becomes the fixed target. That is, the image of the transmitting portion of the liquid crystal display element illuminated by the backlight 124 is reflected by the beam splitter 126, passed through the photo taking lens 105, the focal lens 104, the diaphragm 103 and the wavelength separation mirror 131, is reflected by the sub mirror 102 and the main mirror 101, and projected to the eye fundus from the pupil Ep. By actuating rotationally the main mirror 101 and the sub mirror 102 in accordance with the alignment of the pupil, a position for projecting the fixed target is also changed. However, since the position of the fixed target to the image pickup element is not changed, a photo taking range is not changed while the person to be examined gazes the fixed target. That is, a position representing the fixed target on the image pickup element always corresponds to approximately a position of the macula lutea of the eye. Thus, by changing the deflection angles of the main mirror 101 and the sub mirror 102, the alignment between the pupil and the photo taking optical axis can be performed without changing a photo taking range.

The operator adjusts an operation distance between the eye and the optical system such that a contrast of a pattern of an iris on the front eye portion image displayed on the display unit 112 is suitable. Also, the operator determines focusing, a photo taking range, a flare, a cilia and the like by observing the eye fundus image.

After the above photo taking preparation is completed, the operator operates the photo taking switch 123 to perform static photo taking. When a command inputted by the photo taking switch 123 is detected by the controller 114, it inserts the filter 121 for cutting off infrared light into an optical path, causes the image pickup elements 107r, 107g and 107b to start light storage, and outputs a light emitting signal to the stroboscopic circuit 127 to perform photo taking. The stroboscopic circuit 127 which receives the light emitting signal outputs a trigger signal to the stroboscopic light source 119 for light emitting due to discharge of electric charge charged in the first capacitor 127a. Similar to the case of the above observation light, light flux from the stroboscopic light source 119 is passed through the aperture of the stop 120 having the ring shaped aperture, and infrared light of the light is cut off by the filter 121. The remaining visual light is passed through the relay lens 122, reflected to the left by a mirror portion located in the vicinity of the diaphragm 103, and passed through the sub mirror 102 and the main mirror 1 to illuminate the eye fundus Er from the pupil Ep.

The light from the illuminated eye fundus is reversed in the same optical path, and passed through the diaphragm 103, the focal lens 104 and the photo taking lens 105, is incident into the color separation prism 106 to separate the light into red, blue and green. An eye fundus image is imaged in each of the image pickup elements 107r, 107g and 107b. The amplifiers 108r, 108g and 108b amplify the signals from the image pickup elements 107r, 107g and 107b by predetermined amplification factors for each color to adjust color balance. These signals are converted into digital image data by the A/D converters 109r, 109g and 109b, and stored in the image memories 109rm, 109gm and 109bm. The image data is corrected with respect to image distortion by the image processor 110 in accordance with a correction pattern stored in the memory 110a. The corrected image data is recorded in the recording medium 113a by the storage device 113, simultaneously written in a portion of the video RAM 111 corresponding to the area 112a of the display unit 112, and thus displayed on the area 112a of the display unit 112. After the photo taking is completed, the controller 114 causes the main mirror 101 to return to an initial position and causes an infrared light cutoff filter 121 to be removed from the optical path.

(Third embodiment)

Figure 7:
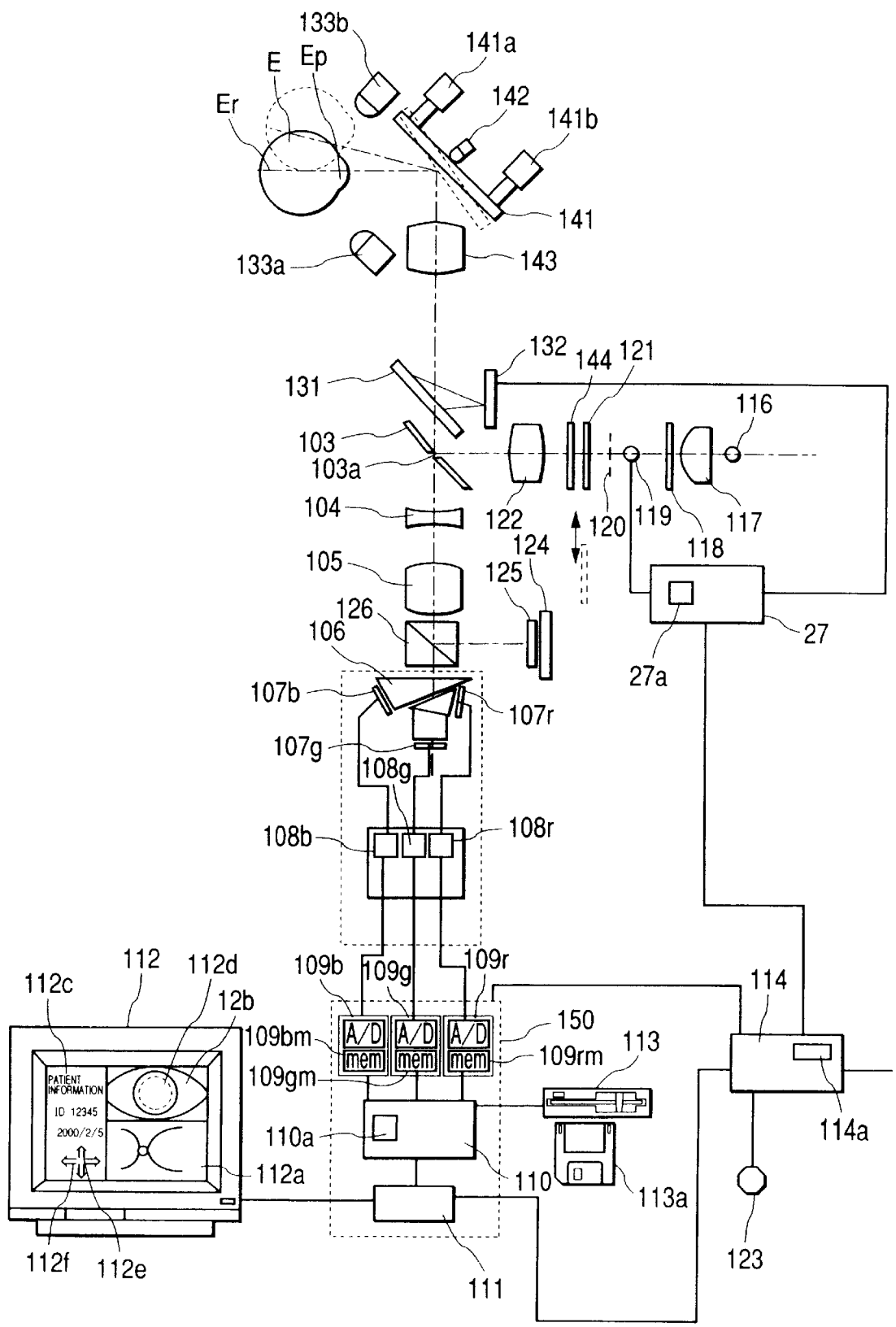
FIG. 7 is a structure of an eye fundus camera according to a third embodiment.
Figure 8:
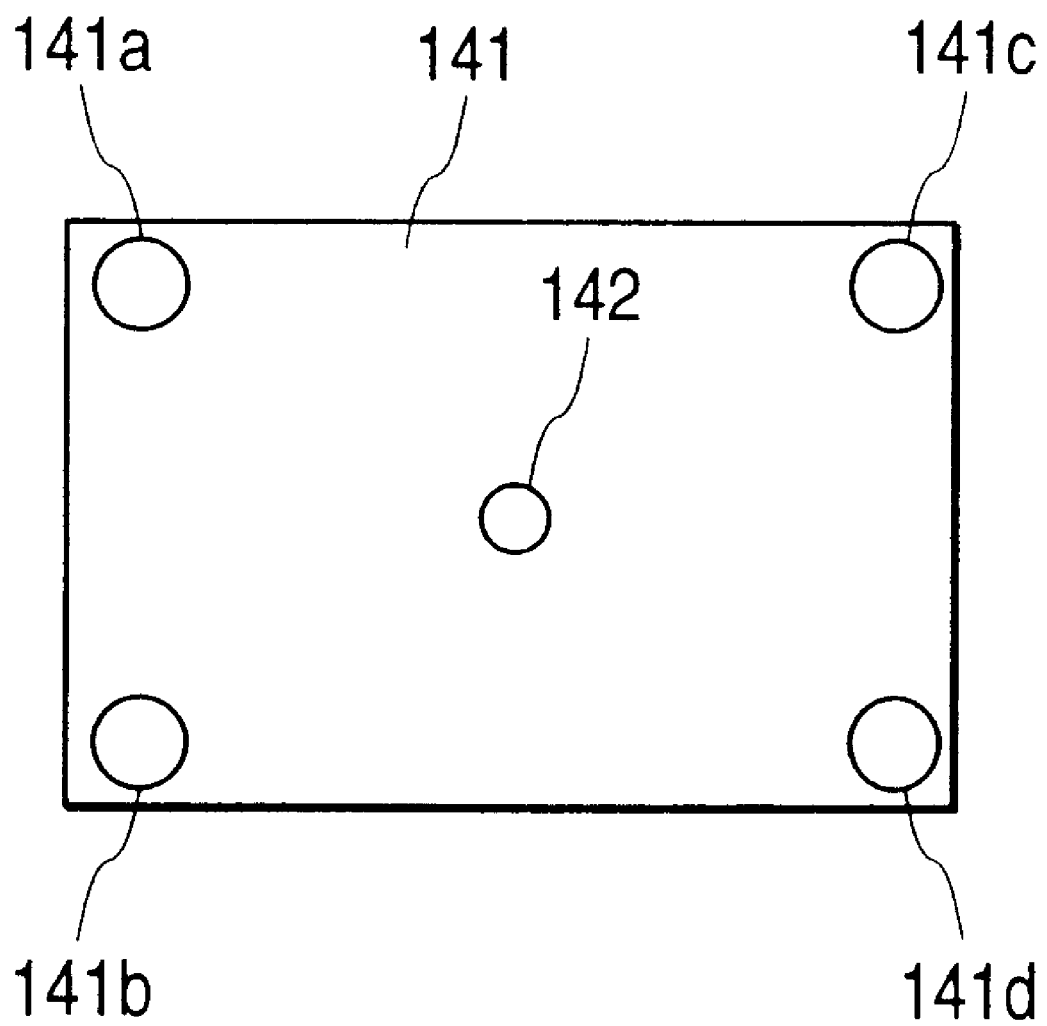
FIG. 8 shows an arrangement of motors in a mirror back surface side.

Although the objective mirror is used in the above examples, as shown in FIG. 7, a reflecting member for position adjustment may be disposed between the objective lens and the eye to perform position adjustment by adjusting the angles of the mirrors. In FIG. 7, an adjusting mirror 141 is disposed in front of the eye E, and an objective lens 143 is disposed in a reflecting direction of the adjusting mirror 141, so that images due to a diaphragm and an illuminating stop are projected to the pupil Ep. As shown in FIGS. 7 and 8, a back surface at an optical axis reflection position of the adjusting mirror 141 is supported with a rotation center plunger 142. A reflecting direction of the adjusting mirror 141 can be adjusted three dimensionally by pushing and pulling (similar to the above examples) due to motors 141a, 141b, 141c and 141d each arranged in the four corners of the adjusting mirror 141. Also, a black point plate 144 having a small light shielding portion in a center portion is provided between the mirror 122 and the stop 120 such that reflected light due to the objective lens 143 is prevented to be incident into the image pickup element through the diaphragm 103 as a total reflecting mirror.

Similar to the above examples, the controller 114 detects a position of the pupil based on the signal output from the image pickup element 132. Of the image of the front eye portion illuminated by the illuminating light sources 133a and 133b, the image of the pupil is displayed darkly. This image is binary-processed by software processing, so that a continuous portion with a value lower than a predetermined value is recognized as the pupil. When this portion recognized as the pupil is eccentric upwardly, the controller 114 drives the motors 141a and 141c in a direction pulling the adjusting mirror 141 from a back surface thereof and drives the motors 141b and 141d in a direction pushing the adjusting mirror 141 from the back surface. When the portion recognized as the position of the pupil is eccentric to a right direction, the controller 114 drives the motors 141a and 141b in the direction pushing the adjusting mirror 141 from the back surface and drives the motors 141c and 141d in the direction pulling the adjusting mirror 141 from the back surface, to control an angle of the adjusting mirror 141.

With respect to the above examples, although a direction of manual operation is displayed on the display unit when the eye exceeds an adjusting range due to the mirror, a direction returning a slant of the mirror to an initial neutral position may be displayed as the direction of the manual operation such that alignment can be performed with a state where the mirror is located in the initial neutral position.

(Fourth Embodiment)

Figure 10:
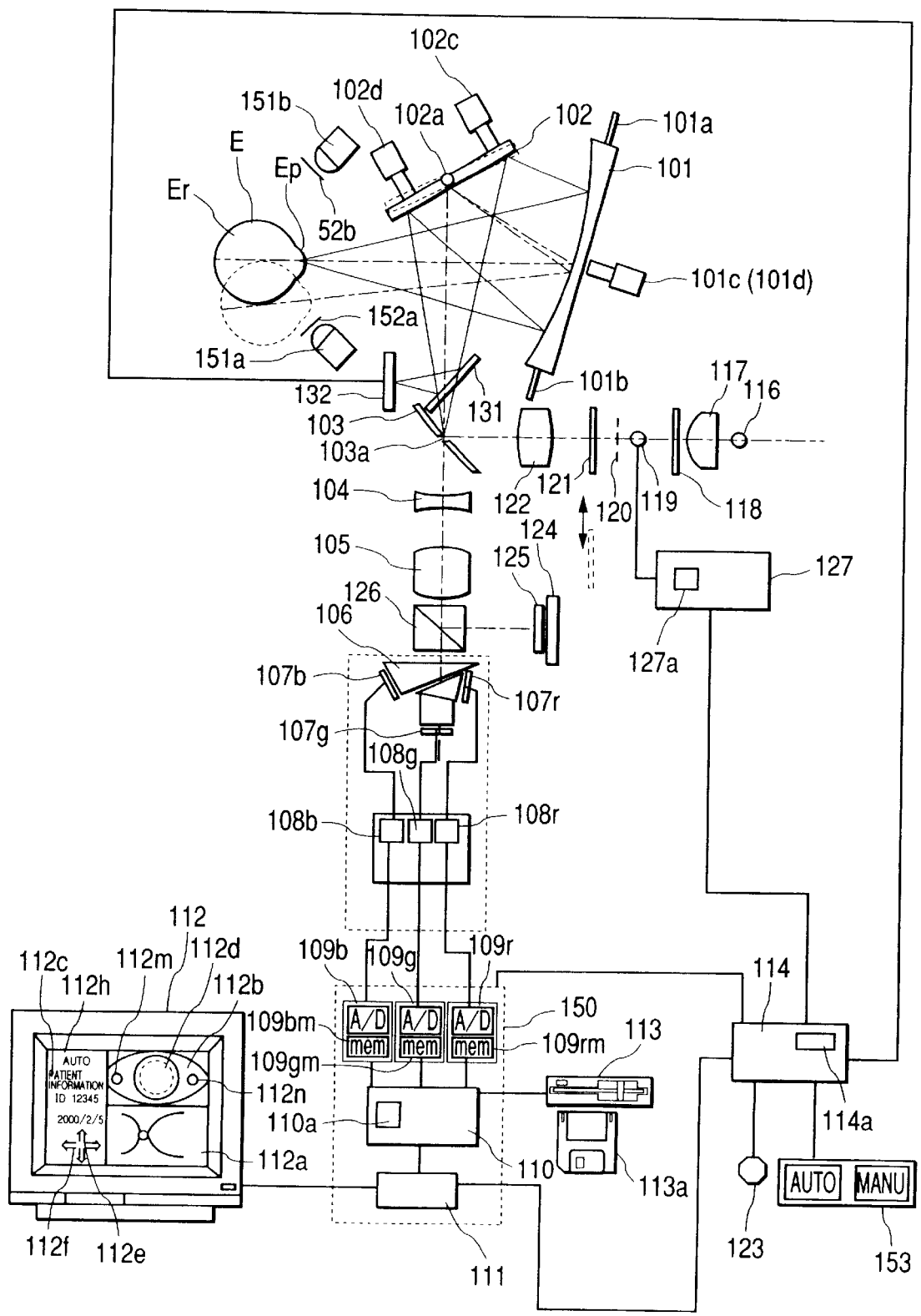
FIG. 10 shows a structure of an eye fundus camera according to a forth embodiment.

Although, with respect to the above embodiment, the position of the pupil is detected by the image pickup element 132 in order to detect the position of the eye, the present invention is not limited to such a detection, an index light flux may be projected to the cornea to detect cornea reflected light of the eye. FIG. 10 shows a structure of a fourth embodiment, and the same references as those in the above embodiments represent the same members. Indexes 152a and 152b are disposed in front of the index light sources 151a and 151b and projected to the front eye portion from two directions. Reflected images of the indexes 152a and 152b are displayed as points (positions) 112m and 112n together with the front eye portion image in a window position 112d on the display unit 112. The controller 114 automatically determines the positions of the reflected images 112m and 112n based on the output signal from the image pickup element 132. Then, the controller 114 controls the angles of the main mirror 101 and the sub mirror 102 so as to enter the reflected images 112m and 112n into a predetermined position, so that automatic alignment is performed in accordance with the movement of the eye. Thus, by projecting the indexes and utilizing reflected light thereof, an effect due to external light becomes small, and alignment can be performed with high precision.

Although, in the above embodiment, the indexes for alignment are directly projected to the front eye portion, the following may be performed as a further modified example. That is, the indexes are projected near a middle position between the a peak of the cornea and a center of a curvature thereof such that the cornea reflected images due to the indexes are imaged in nearly infinite circle similar to that of the eye fundus. The reflected images of the indexes are photo-taken together with the eye fundus image, and then positions of the reflected images of the indexes are detected by software processing for a photo taking image to detect the movement of the eye. Based on this, automatic alignment may be performed in accordance with the movement of the eye. According to the present example, alignment can be performed without using the front eye portion image, and further sensitive detection by change of a position of the cornea can be performed. Also, by multiplex detection with both the above indexes to be provided, position detection for a wide area and high precision position detection for a narrow area can be performed compatibly.

Now, there are a few persons to be examined in which nystagmus is hard and automatic alignment cannot be performed easily. To enable photo taking in a case with such persons, a mode switching device 153 for switching between an automatic alignment mode and a manual alignment mode is provided. This mode switching device 153 can be switched by the operator. Also, when suitable alignment cannot be performed during a predetermined time in the automatic alignment mode, the automatic alignment mode is switched automatically to the manual alignment mode in the mode switching device 153. At this time, for example, a mode display ("AUTO" or "MANUAL") such as 112h is displayed on the display unit 112 such that the operator can determine an alignment mode easily. Naturally, the mode switching device 153 can also be applied to the above embodiments as shown in FIGS. 6 and 7.

Advantages of the apparatus mentioned above is as follows:

(1) By changing angles of the objective mirrors for automatic position adjustment between the eye and the optical system, automatic position adjustment capable of tracking quick movement of the eye speedily is possible. Also, by this, since the operator can concentrate on other operations during photo taking, the photo taking can be performed efficiently.

(2) Since accurate alignment between a center of the pupil and an optical axis can be performed easily, the eye fundus can be illuminated uniformly without shielding of illumination light by an iris in the case of the eye having a small pupil diameter, so that an image with high quality can be obtained.

What is claimed is:

1. An ophthalmologic apparatus comprising:
   a diaphragm;
   an image taking system, having a mirror system with a deflection mirror, for taking an eye fundus image through the mirror which is disposed in a position nearer to an eye to be examined than to the diaphragm in an optical path; and
   a controller for controlling the image taking system so as to perform image taking plural times by changing directions of the mirror, thereby obtaining a plurality of images for the eye fundus from a plurality of directions.

2. An apparatus according to claim 1, further comprising a light source for leading light to the eye fundus of the eye through the mirror system to illuminate the eye fundus,
   wherein the controller causes the light source to emit light in synchronization with change in angles of the mirror.

3. An apparatus according to claim 2, further comprising an image taking switch,
   wherein, by operating the image taking switch one time, the controller controls the angles of the mirrors to be set into two angles to thereby project images of the diaphragm onto two points on a pupil of the eye in succession, and performs light emitting control for the light source in accordance with positions of the two points.

4. An apparatus according to claim 1, wherein the mirror system has a first mirror as the deflection mirror and a second mirror, and the first mirror can be deflected about a rotation axis as a standard.

5. An apparatus according to claim 4, wherein the first mirror has a concave reflection surface for imaging a reflected image of the diaphragm by the second mirror onto the vicinity of a pupil of the eye.

6. An apparatus according to claim 5, wherein the rotation axis, an optical axis of incident light which is incident to the first mirror from the second mirror, and an optical axis of reflected light which is reflected by the first mirror toward the pupil are included in the same plane, and an angle formed by the rotation axis and the optical axis of the reflected light is approximately a right angle.

7. An apparatus according to claim 1, wherein the image taking system has an image pickup element, further comprising:
   a storage device for storing image information in accordance with signals from the image pickup element; and
   a display for displaying an image taken by the image pickup element.

8. An apparatus according to claim 1, further comprising a stereo display for displaying the eye fundus image as stereo information in accordance with a plurality of images taken from the plurality of directions.

9. An apparatus according to claim 1, further comprising a mode selector for selecting either stereophotography or monophotography as a mode, wherein the controller sets the number of photo taking in accordance with the selected mode.

10. An apparatus according to claim 1, wherein the mirror system has a first mirror as the deflection mirror rotatable about a rotation axis as a standard and a second mirror to be fixed, the first mirror has a concave reflection surface for imaging a reflected image of the diaphragm by the second mirror onto a pupil of the eye, the rotation axis of the first mirror, an optical axis of incident light which is incident to the first mirror from the second mirror, and an optical axis of reflected light which is reflected by the first mirror toward the eye to be examined are included in the same plane, an angle formed by the rotation axis and the optical axis of the reflected light is approximately a right angle, and a reflection surface of the first mirror is slanted with respect to the rotation axis, and a cross point between the reflection surface and the rotation axis is aligned with the optical axis of the incident light.

11. An ophthalmologic apparatus comprising:

a diaphragm;

a image taking system, having a mirror system with a deflection mirror, for taking an eye fundus image through the mirror which is disposed in a position nearer to an eye to be examined than to the diaphragm on an optical path;

a light source for leading light to the eye fundus of the eye through the mirror to illuminate the eye fundus;

a detector for detecting movement of the eye; and a controller for controlling deflection of the mirror in accordance with a detected result of the detector, wherein the controller causes the mirror to deflect such that an image of the diaphragm is aligned to a pupil of the eye.

12. An apparatus according to claim 11, the mirror system provides deflection with two degrees of freedom.

13. An apparatus according to claim 12, wherein the mirror system has a first mirror and a second mirror, the first mirror can be deflected about a predetermined direction as a rotation axis and has a concave surface as a reflection surface, and the second mirror can be deflected about a different direction from the predetermined direction as a rotation axis.

14. An apparatus according to claim 13, wherein the reflection surface of the first mirror has a curved surface, and the first mirror can be deflected as a rotation axis about a straight line which is formed by a plane having two focal points and an optical axis and a tangent plane in a contact point between the curved surface and the optical axis, and the second mirror can be deflected as a rotation axis about a straight line which is vertical to a plane having an optical axis reflected by the second mirror and passes a reflection point of the optical axis.

15. An apparatus according to claim 11, further comprising a system for indicating a fixed target to the eye through the mirror.

16. An apparatus according to claim 11, further comprising a system for detecting movement of the eye in accordance with a position of the pupil detected by the detector.

17. An apparatus according to claim 11, further comprising a system for detecting movement of the eye in accordance with a cornea reflected image of an index projected to the eye, detected by the detector.

18. An apparatus according to claim 11, wherein the image taking system has an image pickup element, further comprising:

a storage device for storing image information in accordance with signals from the image pickup element; and a display for displaying an image taken by the image pickup element.

19. An apparatus according to claim 11, further comprising a mode switch for switching between an automatic alignment mode and a manual alignment mode.

20. An apparatus according to claim 19, wherein the mode switch switches from the automatic alignment mode to the manual alignment mode automatically when suitable alignment is not performed during a predetermined time.

* * * * *

UNITED STATES PATENT AND TRADEMARK OFFICE
CERTIFICATE OF CORRECTION

PATENT NO.     : 6,585,374 B2
DATED          : July 1, 2003
INVENTOR(S)    : Kazuhiro Matsumoto It is certified that error appears in the above-identified patent and that said Letters Patent is hereby corrected as shown below:

Column 14,
Line 26, "leading light to" should read -- illuminating --.

Column 15,
Line 30, "leading light to" should read -- illuminating --.

Column 16,
Line 4, "different direction" should read -- direction different --.

Signed and Sealed this

Twenty-first Day of October, 2003

JAMES E. ROGAN
*Director of the United States Patent and Trademark Office*